United States Patent [19]

Wise

[11] 3,978,203

[45] Aug. 31, 1976

[54] SUSTAINED RELEASE OF PHARMACEUTICALS FROM POLYESTER MATRICES

[75] Inventor: Donald L. Wise, Belmont, Mass.

[73] Assignee: Dynatech Corporation, Burlington, Mass.

[22] Filed: July 12, 1974

[21] Appl. No.: 487,886

[52] U.S. Cl. ................................ 424/22; 128/260; 128/335.5; 424/19; 424/32; 424/33; 424/78; 260/75 R

[51] Int. Cl.² .................. A61K 9/22; A61K 31/74

[58] Field of Search .................. 128/260, 335.5; 424/19–22, 78–83, 32, 33; 260/750 R, 78.5

[56] References Cited

UNITED STATES PATENTS 3,737,521  6/1973  Born ................................... 424/22

*Primary Examiner*—Shep K. Rose
*Attorney, Agent, or Firm*—Cesari and McKenna

[57] ABSTRACT

A novel class of polymer-based products for use in physiological environment, e.g. for use as sutures or implanted, medicine-bearing compositions for use in controlled-rate medication, or the like. The advantageous polymers on which these products are based are condensation polymers formed of Krebs cycle acid-type compounds and a physiologically-tolerable polyol type compound such as glycerol or the like.

8 Claims, No Drawings

SUSTAINED RELEASE OF PHARMACEUTICALS FROM POLYESTER MATRICES

BACKGROUND OF THE INVENTION

It has previously been known to use polyamino acid-type materials and polyglycolic acid-type materials (for example, polylactides) for use in physiological environments, especially for sutures which degrade into physiologically-tolerable degradation products. Some of these materials have been suggested for use as medicinal implants. However, it has proved difficult or impossible to achieve both relatively short-term and straight-line release-rate characteristics from matrices formed of such polymer products. Moreover, these products are relatively expensive.

Therefore, the problem facing the present inventors was one of providing physiologically-tolerable polymers which could be advantageously utilized in making improved products for use in physiological environments.

SUMMARY OF THE INVENTION

It is an object of the invention to provide novel compositions which have particular utility in sustained delivery of active medicinal agents in a physiological environment.

Another object of the invention is to provide novel polymeric materials useful as matrices with the medicinal agents to form the compositions of the inventions.

A further object of the invention is to provide sustained-delivery compositions of the type wherein the matrix is metabolized or degraded to an excretable form utilizing the Kreb's Cycle, i.e. the so-called "citric acid cycle" or "tri-carboxylic acid (TCA) cycle."

Another object of the invention is to provide a novel process for making medicinal articles for use in sustained-delivery applications.

Still another object of the invention is to provide a novel class of polymers.

A further object of the invention is to provide polymer-based medicinal articles which are exceptional in their ability to release, at an unusually constant rate, medicinal compounds which are incorporated within the polymer.

Other objects of the invention will be obvious to those skilled in the art on their reading of the instant disclosure.

The above objects have been achieved by the manufacture and utilization of polyester matrices or or polyamide matrices based on the reaction of the di- and tri-carboxylic acids of the type which occur in the Krebs cycle. These acids include citric, cis-aconitic, isocitric, α-ketoglutaric, succinic, fumaric, malic, and oxaloacetic. The preferred procedure is to react these acids or the physiologically tolerable homologues thereof with a biologically compatible polyol compound, e.g. glycerol, or a compound based on such a polyol, e.g. an ester of glycerol. Among the physiologically tolerable polyols useful in the invention are glycerol, mannitol, sorbitol, and the like, but glycerol and and glycerol-derived compounds are preferred reactants.

The molecular weights of polymers of the invention are usually between 20,000 to 200,000. Some limited crosslinking is usually present and, in all cases, the polymer is a solid material capable of assuming shape and maintaining its structural integrity, i.e. not disintegrating, in the physiological environment during its useful release-moderating life. Thereafter, it degrades to products which are readily disposed of by normal bodily functions.

Among the reactions which may be utilized in forming compositions according to the invention are those wherein the Krebs-acid compound is reacted with a triester such as triacetin, or with a monoester such as monoacetin, or with glycerol itself. The Krebs-acid compound may be utilized in any convenient form, e.g. in the form of an anhydride, a diacid chloride, in a salt form such as the di-sodium salt form, or the like.

The precise reaction may be selected in view of the ease with which it permits production of polymer of desired properties. In general, a triester such as triacetin is less reactive and can be advantageously used to produce flexible or relatively low molecular weight products. There are other procedures which are useful in optimizing preparation of the polymers. When utilizing monoesters like the monoacetins, it is believed to be desirable to select one wherein the two hydroxyl groups have similar reactivity, e.g. as in β-monoacetin. Such a procedure will allow one to obtain longer linear polymers. Moreover, when glycerol is used as a reactant, maintenance of the reaction temperature below about 180°C will tend to suppress undesired reactions with hydroxyl groups other than the primary hydroxyl groups. Moreover, it is sometimes advantageous to utilize the diacid form of the Krebs-cycle compounds to avoid water of reaction being formed and to lower the polymerization temperatures. Interfacial polymerization appears to be a particularly desirable approach to preparing polymers with the diacid compounds.

However, it should be realized that the general technology for forming condensation polymers of polyols and polyacid is very well known to those skilled in the art. The primary contribution of the present inventors is the selection of polymeric building blocks such that, on decomposition of the polymer in a physiological environment, the degradation products will be easily disposed of by the body. Moreover, it has been discovered that these polymers, when utilized as matrices of pre-selected shapes, provide means to form compositions from which medicines (and by the term "medicine" is meant treating agents generally) can be released in the body at a surprisingly stable and predictable rate over relatively short time periods. For example, it is possible to deliver 75 to 90 percent or more of a medicine within a 30-day treatment period with a substantially constant release rate, i.e. a release rate which does not differ from a ± 10 percent delivery rate during that period.

ILLUSTRATIVE EXAMPLE OF THE INVENTION

In order to point out more fully the nature of the present invention, the following working example is given as an illustrative embodiment of the present process and products produced thereby.

In the following examples, the material known as hydrocortisone (11β, 17α, 21-trihydroxy-4-pregnene-3, 20-dione) was used as an active agent because there appears to be substantially no chemical interaction between the treating agent and the polymeric matrices illustrated, it is believed that those skilled in the art can interpret the examples as illustrative of treating agents generally.

The active agent was dissolved in ethyl alcohol, and a known amount of radioactive-carbon-tagged hydrocortisone was added to the solution. The solvent was evaporated to yield an active agent of uniform radioactive concentration. This agent was comminuted and the resulting finely-divided active agent blended with polymer in a jar mill. The resulting uniform blend was sintered or mulled into shaped medicinal articles. Sintering is merely a fusing of drug and polymer with heat and pressure, usually at temperatures from about 150° to about 200°C. Mulling was used where the polymer was soft enough to form a cohesive mixture using only the mulling action.

In Vitro Testing of Physiological-Release Characteristics

The samples prepared were weighed and placed in 50 ml. of an aqueous solution buffered to a pH of 7 with monobasic and dibasic potassium phosphates (i.e. with Sorenson's buffering solution). The liquid was agitated and maintained at 37°C. Samples of the liquid were removed from time to time and were evaluated by radioactive scintillation analysis to determine the amount of cortisone released.

EXAMPLE 1

The following procedure is followed in preparing a polymer from fumaric acid and α-monoacetin by solution polymerization.

A 2000 ml., round-bottom flask is enclosed in an electric heating mantle and equipped with means to pass nitrogen purge gas over its contents. The flask is also equipped with a Dean Stark trap, a reflux condenser, and a bubbler to aid in regulating nitrogen flow.

The flask was charged with 100 ml. of dimethylformamide (DMF) for use as a solvent reaction medium. The solvent is refluxed at 153°C until the Dean Stark trap is full to assure the absence of water in the system. After an hour at reflux, the solvent was cooled to 50°C. Then the reactants are added to the solvent.

| Fumaric acid | 10 grams |
| Monoacetin | 9.57 grams |
| Potassium methoxide | 0.1 grams |

The mix was allowed to reflux for 5 hours and 25 minutes at 153°C. A clear, pale yellow solution formed during this period. It was soluble in water and insoluble in hexane. When the DMF was distilled from the solution over a period of about 3 hours, a brown solid condensation polymer of fumaric acid and monoacetin was left in the flask.

EXAMPLE 2

A polymer of L-Malic acid and monoacetin was also prepared by a suspension, sometimes called "pearl," polymerization method. The "solvent" used as the suspending medium was Stoddard solvent, the catalyst was potassium methoxide, and the reaction temperature was 150°C.

The charge to the reactor, made after the medium reached temperature, was as follows:

| Stoddard solvent | 120 ml. |
| Malic Acid | 10 grams |
| Monoacetin | 8.3 ml. |
| Potassium methoxide | 0.1 grams |

The catalyst was added last. The reaction was carried out for 6 hours at about 150°C and under continuous agitation.

The polymer was recovered by distilling of excess solvent, filtering, washing with hexane, air drying, and then placing under a vacuum for several hours. A tacky pliable polymeric solid was recovered and identified as a polyester resin.

EXAMPLE 3

A pearl polymerization similar to that described in Example 2 was carried out but using the following reaction mix:

120 ml. of silicone oil
10 grams of citric acid
5.34 ml. monoacetin
0.465 ml. N-butyl lithium The reaction was run for about 2.5 hours at 145°C. A sticky, yellow polyester polymer was recovered.

EXAMPLE 4

A quantity of 0.82 grams of the polymer of Example 3 was mulled with 0.1655 grams of $^{14}$C-labelled hydrocortisone; 0.261 grams of the resulting composition was shaped in the form of a football-shaped pellet and placed in an extraction thimble for in vitro testing. See FIG. 1 for a curve descriptive of the release rate.

EXAMPLE 5

A quantity of 0.35 grams of the polymer of Example 3 was mulled with 0.175 grams of $^{14}$C-labelled hydrocortisone; 0.259 grams of the resulting composition were shaped in the form of a football-shaped pellet and placed in an extraction thimble for in vitro testing. See FIG. 2 for a curve descriptive of the release rate.

EXAMPLE 6

The following procedure was carried out in preparing a condensation product from succincic anhydride and glycerol A round-bottom, 250 ml. indented flask was equipped as described in Example 1 but also with a stirrer. A quantity of 120 ml. of silicone oil was charged to the flask. To the silicone reaction medium was added:

10 grams of succinic anhydride
7.3 grams of glycerol
0.05 grams of paratoluene sulfonic acid The temperature was raised rapidly to 163°C. The reaction continued for 1.5 hours at 163°C. Then the temperature was lowered to 90°C for two more hours and the stirring was continued. After this time the contents of the flask were cooled, and the reaction product, in the form of small yellow polymeric pearls of about 1/10 inch in diameter, was filtered, washed with hexane, air dryed, and put under vacuum overnight.

EXAMPLE 7

A quantity of 0.919 grams of the polymer of Example 6 was mulled with 0.229 grams of labelled hydrocortisone; a sample of 0.6283 grams of the resulting composition was shaped as a football-shaped pellet preparatory to in vitro testing. See FIG. 1 for a curve descriptive of the release rate.

EXAMPLE 8

A quantity of 0.316 grams of the polymer of Example 6 was mulled with 0.1810 grams of labelled hydrocortisone. A sample of 0.2702 grams of the resulting composition was shaped into the form of a football-shaped pellet. See FIG. 2 for a curve descriptive of the release rate of the hydrocortisone.

It is also to be understood that the following claims are intended to cover all of the generic and specific features of the invention herein described and all statements of the scope of the invention which might be said to fall therebetween.

What is claimed is:

1. A shaped implantable solid article, formed of a composition comprising a pharmaceutical agent, in a matrix, said pharmaceutical agent being adapted for controlled diffusion from said matrix upon implantation, said matrix being formed essentially of a polyester, having an average molecular weight of up to 200,000 formed by the polymerization of a first reactant which is monoacetin, triacetin, glycerol, mannitol, or sorbitol with (2) at least one of a second reactant which is fumaric acid, L-malic acid, citric acid cis-aconitic acid, isocitric acid, alpha-ketoglutaric acid, succinic acid, oxaloacetic acid, or the anhydrides, acid chlorides or disodium salts of said acids.

2. An implantable article as defined in claim 1 having a consistent diffusion rate of said pharmaceutical agent from said matrix until less than about 10 percent of said agent remains within said matrix.

3. An implantable article as defined in claim 1 wherein said polyol is triacetin or monoacetin.

4. A composition as defined in claim 2 wherein said second compound is citric acid, or succinic acid.

5. An implantable article as defined in claim 4 wherein said polyole is triacetin or monoactin.

6. An implantable article as defined in claim 3 wherein said pharmaceutical agent is a steroid.

7. A composition as defined in claim 5 wherein said second compound is citric acid or succinic acid.

8. An implantable article as defined in claim 5 wherein said pharmaceutical agent is a steroid.

* * * * *